(12) United States Patent
Bae et al.

(10) Patent No.: US 6,204,242 B1
(45) Date of Patent: Mar. 20, 2001

(54) METHOD FOR TREATING RHEUMATOID ARTHRITIS WITH COMPOSITION CONTAINING HISTONE

(75) Inventors: Insoo Bae, Daejon; Dong-soo Kim, Seoul; Heajoon Yim, Daejon; Neon-Cheol Jung, Daejon; Yong-Weon Yi, Daejon; Seung-Suh Hong, Daejon; Hyun-Soo Lee, Seoul, all of (KR)

(73) Assignee: Samyang Genex Corporation, Seoul (KR)

( * ) Notice: Subject to any disclaimer, the term of this patent is extended or adjusted under 35 U.S.C. 154(b) by 0 days.

(21) Appl. No.: 09/381,559
(22) PCT Filed: Jan. 23, 1999
(86) PCT No.: PCT/KR99/00037
§ 371 Date: Jan. 19, 2000
§ 102(e) Date: Jan. 19, 2000
(87) PCT Pub. No.: WO99/37318
PCT Pub. Date: Jul. 29, 1999

(30) Foreign Application Priority Data

Jan. 24, 1998 (KR) .................................................. 98-3362

(51) Int. Cl.⁷ .................................................. A61K 38/00
(52) U.S. Cl. .................................................. 514/2
(58) Field of Search .................................................. 514/2

(56) References Cited

U.S. PATENT DOCUMENTS

| | | | | |
|---|---|---|---|---|
| 4,818,763 | * | 4/1989 | Rusch et al. | 514/2 |
| 5,182,257 | * | 1/1993 | Zeppezauer et al. | 514/2 |
| 5,714,462 | * | 2/1998 | Davies et al. | 514/8 |
| 5,780,432 | * | 7/1998 | Zeppezauer | 514/12 |
| 5,905,083 | * | 5/1999 | Cincotta et al. | 514/288 |
| 6,015,790 | * | 1/2000 | Barlozzari et al. | 514/17 |

* cited by examiner

*Primary Examiner*—James H. Reamer
(74) *Attorney, Agent, or Firm*—Darby & Darby

(57) ABSTRACT

The present invention relates to a novel use of histone and provides a pharmaceutical composition containing histone as an active ingredient to improve the symptoms of progressive, inflammatory and autoimmune arthritis. The pharmaceutical composition of the present invention includes histone, especially histone H1 as an active ingredient, and could include pharmacologically approved carriers if necessary. Histone H1 lowered induction of arthritis and reduced arthritis index more effectively than steroidal dexamethasone and also had a significant preventive effect.

6 Claims, 6 Drawing Sheets

(3 of 6 Drawing Sheet(s) Filed in Color)

METHOD FOR TREATING RHEUMATOID ARTHRITIS WITH COMPOSITION CONTAINING HISTONE

TECHNICAL FIELD

The present invention relates to the use of histone H1 in improving inflammatory symptoms of arthritis. Histone H1 lowers an induction of arthritis and reduces arthritis index more effectively than conventional drugs and also has a significant preventive effect.

BACKGROUND OF THE INVENTION

The present invention relates to a biologically active compound and compositions containing the same to improve symptoms of progressive, inflammatory and autoimmune arthritis. Despite the development of many arthritis drugs, arthritis remains to be a world wide serious disease due to an increasing aging population. Even though the death rate due to arthritis is low, the quality of life of an individual who suffers from this disease is sacrificed with lowered activity level and productivity.

Among many types of arthritis, the most significant one is rheumatoid arthritis. Rheumatoid arthritis is an autoimmune disease by the action of auto-reactive T lymphocytes. T lymphocyte causes rheumatoid anthritis via delated type hypersensitivity. It is not fully understood which antigen is recognized by T lymphocyte to cause this disease. Type II collagen is known to be the most probable one, but other possibilities cannot be excluded. Anti-histone autoantibody has been discovered even though it is not clear that this antibody is the cause of the disease.

Many drugs have been used to treat rheumatoid arthritis without a complete relief of the symptoms. Conventional drugs include non-steroidal anti-inflammatory drugs (NSAIDs, aspirin, ibuprofen), gold salt, penicilamine, and steroidal hormones. The steroidal hormone, which is most potent and effective, have side effects when taken for a long period. Recently, recombinant soluble receptor of tumor necrosis factor (TNF), that play a major role in the inflammation mechanism, is on trial for new treatments of rheumatoid arthritis. However, an improved formulation to treat symptoms of rheumatoid arthritis such as inflammation, edema, abnormal formation of new blood vessels, destruction of cartilage and bone erosion is required.

Collagen-induced arthritis (CIA) has been used as an animal model of the T-lymphoidal rheumatoid arthritis (Autoimmunity to Type II collagen: Experimental model of arthritis, J. Exp. Med. 146; 857–868 (1977)). When type II collagen was injected into mice, which are prone to develop arthritis, arthritis was induced within 2 weeks with symptoms such as formation of pannus, erosion of cartilage and bone. Like the rheumatoid arthritis, CIA also has the humoral and the cellular immune responses against collagen.

Histone is one of the major nuclear components in the cells and forms chromosomes with nucleic acids. Many different forms of histones (H1) were isolated from mammals other than humans. There are many reports regarding various physiological activities of histone H1.

The discovery and isolation of water-soluble histone H1 in bovine plasma and milk was reported in Biochem. J. Vol. 244, 675–682, 1987. Proc. Natl. Acad. Sci. U.S.A. vol. 82, 4871–4875, which reported that the major component of the homeostatic thymus hormone (HTH) is histone H1. Histone H1 circulates freely in the lymph and blood vessels and acts similar to hormones by having capabilities such as controlling the secretion of other hormones.

Ann. J. Med. Sci. vol. 250, 79–85, 1965 also reported that the HTH therapy could potentiate the immune system and resolve the immunological problems associated with thymectomy. WO 8503003A suggests using histone H1 fragment, which has the characteristics of thymus hormone, as an immunotherapy to prevent leukemia after thymectomy or radiotherapy of thymus. U.S. Pat. No. 5,182,257 disclosed histone H1, H2A, H2B, H3 and H4 as drugs for lymphoma or leukemia.

Chemical abstracts 74,85743 (1971) reported that, when taken together with T2 bacteriophage, histone H1 subunit could down-regulate the formation of antibodies against T2 bacteriophage. Chemical abstracts 73,96837 (1970) reported the use of histone H1 as an immunosuppressant for skin grafting.

Nature vol. 360, 33–39, 1992 reported that histone H1 can stabilize the flagellar microtubule structure of sea urchin. J. Biol. Chem vol. 259,15523–15531, 1984 reported that histone H1, acting with the microtubules isolated from murine brain, induces aggregation of tubulin which is similar to the ring structure of the microtubules.

No existing references, however, suggests using histone H1 as a drug to treat rheumatoid arthritis.

BRIEF DESCRIPTION OF THE DRAWINGS

The file of this patent contains at least one drawing executed in color. Copies of this patent with color drawing (s) will be provided by the Patent and Trademark Office upon request and payment of the necesary fee.

SUMMARY OF THE INVENTION

Figure 1:
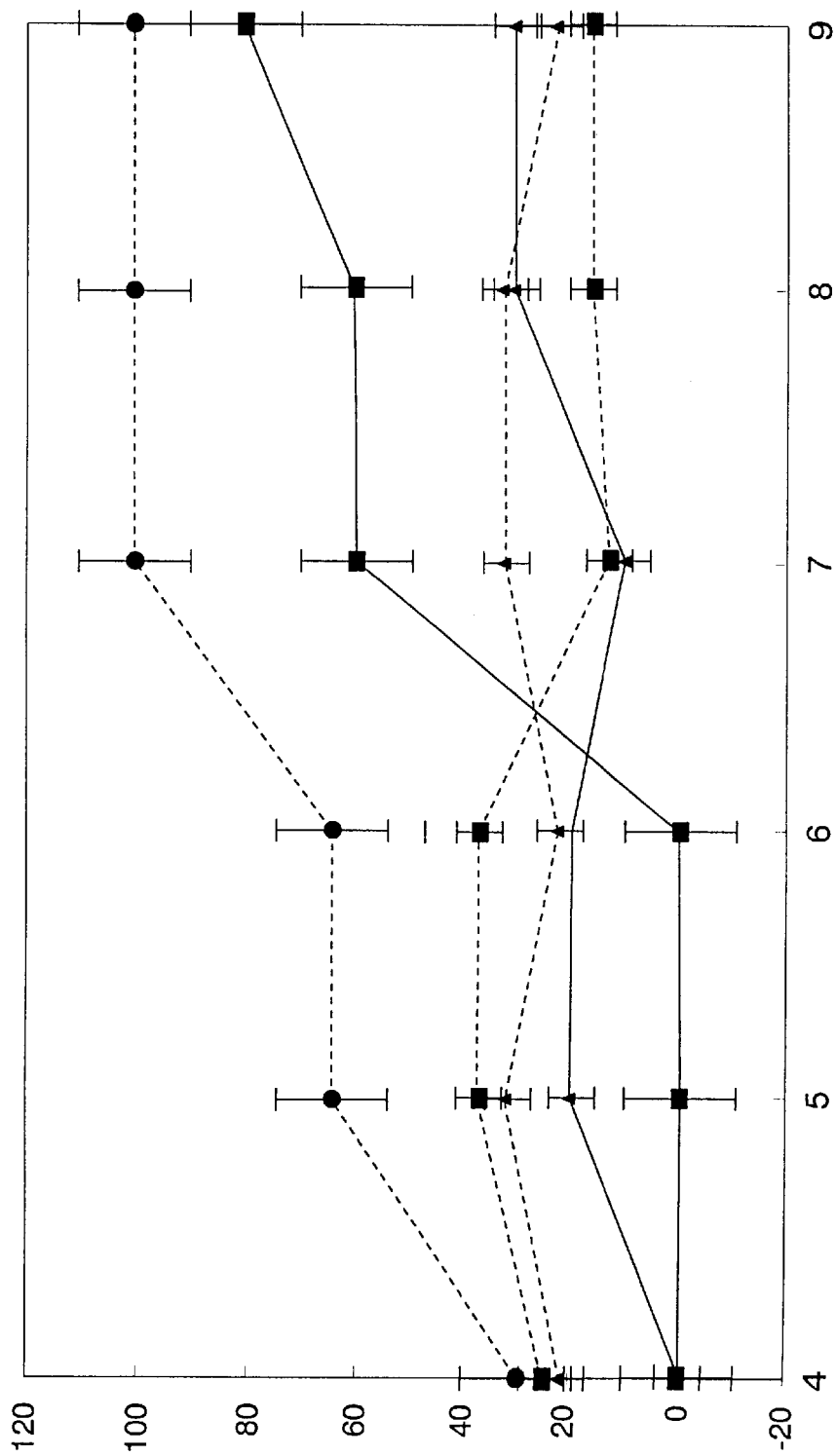
FIG. 1 is a graph showing the changes in the induction of rheumatoid arthritis after administration of histone H1 (l . . . l: no treatment after collagen inoculation (control group), ▲__568 : a group that had dexamethasone for a preventive effect, ▲ . . . ▲: a group that had dexamethasone for a treatment effect, n—n the group that had histone H1 for a preventive effect, n . . . n: a group that had histone H1 for a treatment effect).

It is an object of the present invention to provide a pharmaceutical composition that is more effective than conventional formulations to improve the symptoms of progressive, inflammatory and autoimmune arthritis.

It is an other object of the present invention to provide a pharmaceutical composition containing histone to improve the symptoms of progressive, inflammatory and autoimmune arthritis. It is a further object of the present invention to provide a pharmaceutical composition containing histone to prevent the invasion of progressive, inflammatory and autoimmune arthritis.

It is a further object of the present invention to a method for reducing rheumatoid arthritis symptoms in patients comprising administrating histone in a therapeutic effective amount to said patients.

DETAILED DESCRIPTION OF THE INVENTION

The present invention relates to a novel use of histone and provides a pharmaceutical composition containing histone as an active ingredient to improve symptoms of progressive, inflammatory and autoimmune arthritis.

The symptomatic alleviation includes 1) the improvement of arthritis related symptoms; 2) the prevention of the progress in a progressive disease; and 3) the prevention of invasion in an arthritis prone individual.

The pharmaceutical composition of the present invention comprises histone, especially histone H1 as an active ingredient, and may include pharmacologically approved carriers if necessary.

The pharmaceutical composition of the present invention may be used by itself or a combination with conventional drugs for arthritis.

To determine that the symptoms of autoimmune rheumatoid arthritis could be alleviated by the histone H1 treatment, histone H1 subunit was administered to mammals that were invaded by or prone to arthritis. Collagen induced arthritis, which is a well-known animal model for the rheumatoid arthritis, was induced in experimental mice (EXAMPLE 1). In the present invention, mammals can be extended to human and arthritis can be extended into rheumatoid arthritis. There is no limitation in the origin to isolate histone in the present invention. Also, histone can be extended into histone H2A, H2B, H3 and H4 or a mixture thereof.

Further, the present invention relates to a method for reducing rheumatoid arthritis symptoms in patients comprising administrating histone in a therapeutic effective amount to said patients.

The required amount of histone H1 enough to prevent the symptoms of arthritis will be determined by an ordinary skilled person in the art without undue experiments.

In the present invention, the interval of administration was 3–4 days, but the interval can be extended to 1, 2 or 4 weeks. The ideal means of administration is intravenous or intraperitoneal injection, but other methods can also be used.

The most effective administration route, the amount and the interval of administration could be controlled with ease by observing the degree of symptomatic progress or the reaction of the patient after administration according to the diagnosis or the prescription of a doctor.

The invention will be illustrated further by the following examples, but not limited to the examples given.

To estimate the average values in each experimental group, Student s t-test was used in the examples of the present invention. Chi-square test was used to estimate the standard deviation. The result was considered statistically significant when $p<0.05$.

EXAMPLE 1

Induction of Rheumatoid Arthritis in Experimental Mice

Induction of Arthritis

Five-week old DBA/1J female mice were imported from Charles River Japan and allowed to adapt in an animal room for two weeks before using them in the experiments at the age of 7 weeks (20–25 g).

Isolated and quantified type II collagen of chicken (Sigma Chemical Co., St. Louis, Mo., U.S.A.) was solubilized in 0.1 N acetic acid at a concentration of 2 mg/ml. The solution was mixed with an equal amount of a complete Freund's adjuvant at 4_C to form a suspension. One hundred microliters of this mixture was injected intravenously around the origin of the tail vein and further inoculated at 3 and 6 weeks after the first injection (D. E. Trentham et. al., Autoimmunity to Type II collagen: An Experimental Model of Arthritis, *J. Exp. Med.* 146; 857–868 (1977)). Arthritis was induced from the $4^{th}$ week after the first injection.

Estimation of Arthritis

Clinical incidence of arthritis % (C.I.A) and arthritis index were examined. C.I.A. was expressed as the percentage of mice that have arthritic symptoms among the total mice. The degree of inflammation expressed as the arthritis index was categorized from 0 to 3 by 2 researchers every week as below. Pictures of the feet of some mice were taken 6 weeks after the collagen administration.

0: Normal

1: Slightly swelling and/or erythema

2: Definite edematous swelling

3: Severe edema and joint rigidity

Arthritis index was calculated for 4 feet (2 hind feet and 2 fore feet) giving the maximum value of 12. The index 6–8 was considered severe since collagen induced arthritis invades in general mainly the hind feet.

EXAMPLE 2

Extraction and Isolation of Histone H1

Histone H1 was obtained from Boehringer Mannheim (Catalog Number 223549, lyophilizate, from calf thymus, electrophoretically homogeneous) for the experiment.

EXAMPLE 3

Preventive Effect of Histone H1 Against Arthritis

Administration of Histone H1

As a test group to examine the preventive effect, 1 mg/kg body weight of histone H1 was administered into 10 mice via intraperitoneal injection 2 times every week from the third week (before arthritis induction) up to $10^{th}$ week after the first injection. Histone H1 was diluted at a concentration of 5 mg/ml in PBS. As a comparison group, 1 mg/kg body weight of dexamethasone, current available rheumatoid arthritis drug, was administered into 10 mice via intraperitoneal injection 2 times every week from the third week (before arthritis induction) up to $10^{th}$ week after the first injection. As a control group, 300_l of PBS was administered into 20 mice 2 times every week from the third week up to $10^{th}$ week after the first collagen injection.

Arthritis Induction and Estimation of Arthritis Index

Figure 2A:
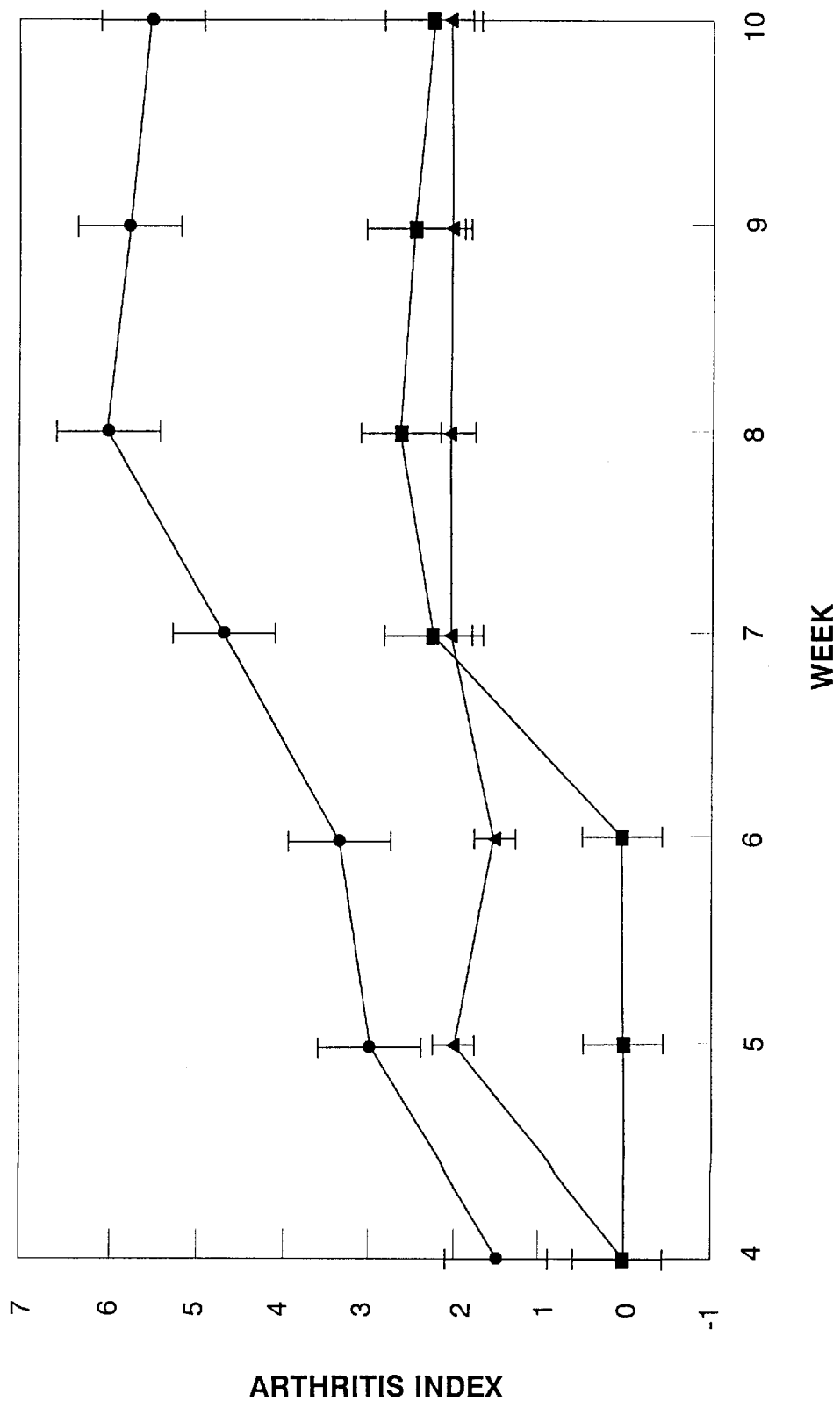
FIG. 2A is a graph showing the preventive effect of histone H1 against rheumatoid arthritis (l . . . l: no treatment after collagen inoculation (control group), ▲__▲: the group that had dexamethasone injection, n—n: a group that had histone H1 injection).
Figure 2B:
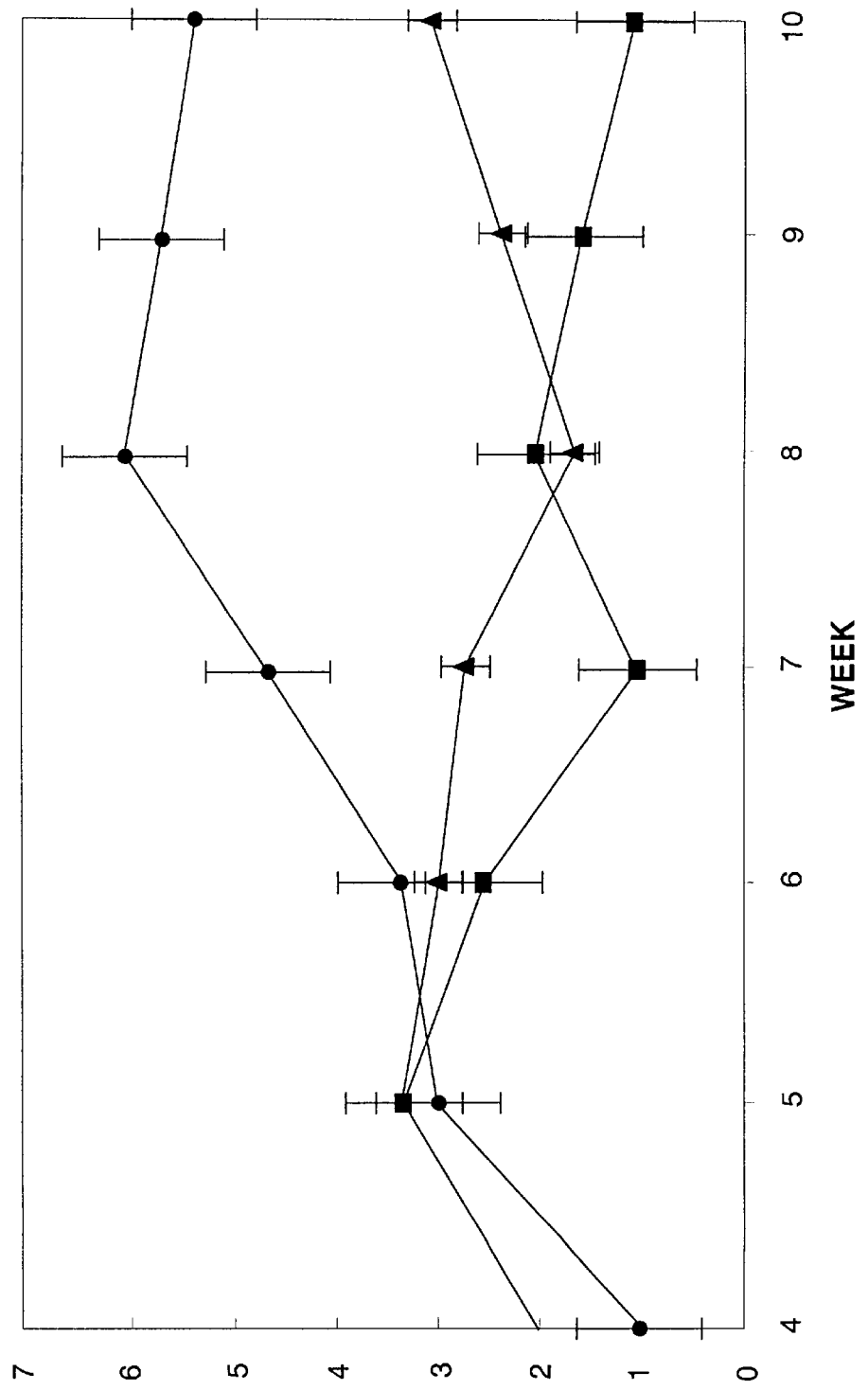
FIG. 2B is a graph showing the treatment effect of histone H1 against rheumatoid arthritis by the changes in arthritis index with time (l . . . l: no treatment after collagen inoculation (control group), ▲__▲: the group that had dexamethasone treatment, n—n the group that had histone H1 treatment).
Figure 3A:
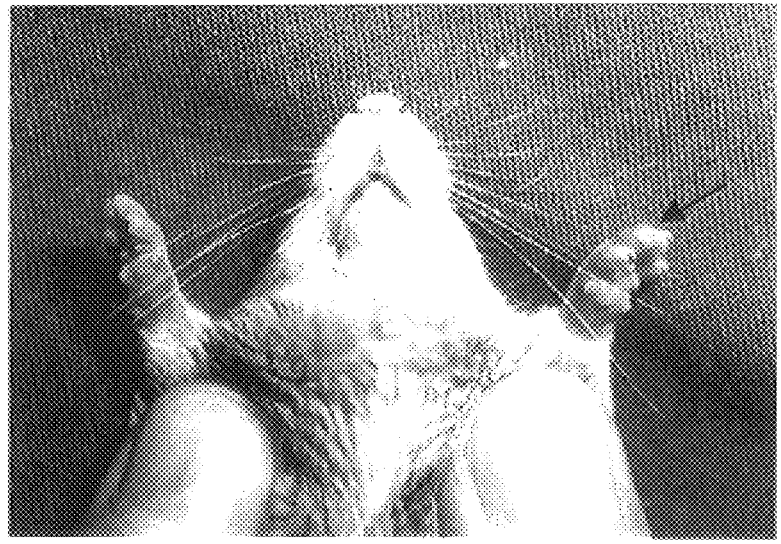
FIG. 3A is a picture of a fore leg of a mouse in the control group showing edema at 6 weeks after collagen inoculation.
Figure 3B:
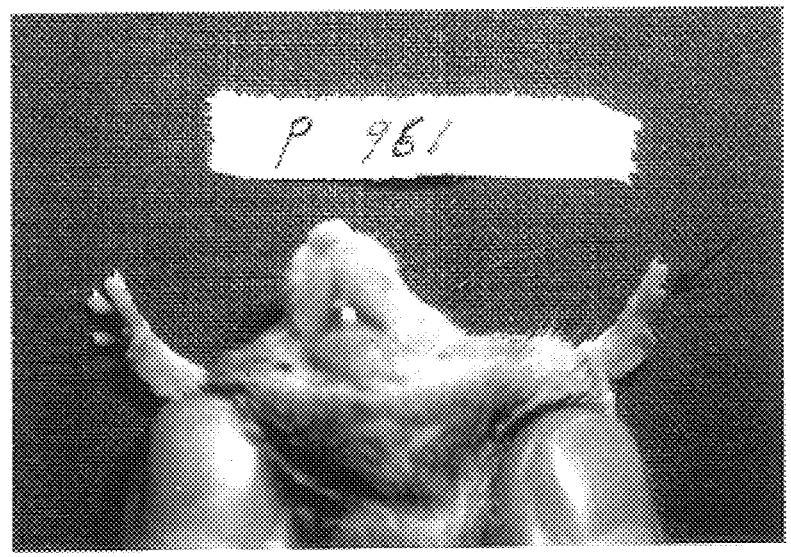
FIG. 3B is a picture of a fore leg of a mouse that had histone H1 administration at 6 weeks after collagen inoculation.

Induction of arthritis was observed 4 weeks after the inoculation of antigens in every group of mice. In the control group that had no treatment after the collagen injection, arthritis induction began 4 weeks after the inoculation (30%). C.I.A. was 64.3% at $5^{th}$ and $6^{th}$ weeks and 100% at the $7^{th}$ week. Compared to this result, the test group of mice that had been injected with histone H1 had a complete prevention of arthritis induction up to the $6^{th}$ week. C.I.A. in the test group was 60% at $7^{th}$ and $8^{th}$ weeks and 80% at the $10^{th}$ week. The comparison group of mice that had been injected with conventional dexamethasone had 20 to 30% of C.I.A. from $4^{th}$ to $10^{th}$ weeks. Arthritis index for the comparison group was severe with the values of 1.50 0.55 in 4 weeks, 3.00 1.00 in 5 weeks and had the maximum value of 6.00 2.05 in 8 weeks after the antigen inoculation (FIGS. 2A and 2B). Compared to this result, arthritis in the test group was first observed at the 7th week after the inoculation having 60% of the arthritis index of the control group. In the mice that had arthritis, the arthritis index was ca. half of the control group with the values of 2.67 1.15 at 8th weeks and 2.25 1.26 at the 10th week showing that the preventive effect lasts longer than 10 weeks. In the case of dexamethasone injected mice, the arthritis index were 2.00 and 1.50 at 5 and 6 weeks, respectively showing that the preventive effect is lower than histone administration up to 6 weeks.

Estimafion of Immune Reaction: Anti-Collagen Antibody Level

At the $10^{th}$ week the serum was isolated from the blood obtained through a heart puncture. The serum was kept at −80_C and thawed immediately before the experiment to measure the anti-collagen antibody level by performing an ELISA (D. E. Tretham & R. A. Dynesius-Trentham, J. Immunol. 130; 2689–2692 (1983)). Type II collagen (25_ g/ml) in 0.1 M PBS was placed in each well of a 96-well polystyrene microplate (Nunc, Denmark) and was incubated at 4_C for 8 hours. After the incubation, the wells were washed several times with a PBS-0.05% Tween 20 solution. To prevent non-specific immune reactions, PBS-0.5% ovalbumin was added in each well and incubated for an hour at room temperature and subsequently washed again with the PBS-0.05% Tween 20 solution. The serum, diluted 500 times with a buffer solution was added in each well and reacted for 2 hours at room temperature and further washed with the PBS-0.05% Tween 20 solution. After reacting each well with alkaline phosphatase conjugated goat anti-mouse IgA and IgM for 2 hours and adding 1 mg/ml of p-nitrophenyl phosphate, the absorbance at 450 nm was measured. The anti-collagen antibody level was measured twice for each sample and averaged.

The anti-collagen antibody level for the test group was 0.588±214 ($p<0.00005$) which was significantly lower than the value of 0.925±075 for the comparison group. The biological significance, however, is not evident since the anti-collagen antibody level was relatively high in every group.

EXAMPLE 4

Arthritis Treatment Effect of Histone H1

Administration of Histone H1

As a test group to examine the treatment effect, 1 mg/kg body weight of histone H1 was administered into 10 mice via intraperitoneal injection 2 times every week from the $6^{th}$ week (after arthritis induction) up to the $0^{th}$ week. Histone H1 was diluted at a concentration of 5 mg/ml in PBS. As a comparison group, 1 mg/kg body weight of dexamethasone, a currently available rheumatoid arthritis drug, was administered into 10 mice via an intraperitoneal injection 2 times every week from the $6^{th}$ week (after arthritis induction) up to the $10^{th}$ week. Identical control group was used as in EXAMPLE 1.

Arthritis Induction and Arthritis Index

C.I.A. in the test group of mice that were treated with histone H1 at the $6^{th}$ week (after arthritis induction) after antigen inoculation was 37.5% at the $6^{th}$ week and was reduced to 12.5% at the $7^{th}$ week. This treatment effect lasted up to the $10^{th}$ week with C.I.A. of 14.3% at $8^{th}$ and $10^{th}$ weeks. In the comparison group that had the dexamethasone treatment, C.I.A. was 22.2%, 33.3% and 22.2% at $7^{th}$, $8^{th}$ and $9^{th}$ weeks, respectively, showing that the treatment effect was better for histone H1 as a whole.

Arthritis index was 3.33 0.58 at the 5th week after the inoculation for the test group that had the histone treatment. After administration of the histone H1 at the 6th week, the C.I.A remained the same as that at the 5th week however had a reduced arthritis index of 2.67 0.58. After the 7th week, ⅔ of the induced arthritis was completely cured. For the mice that still had the arthritis, the arthritis index decreased to 1.00, 200 and 1.00 at 7th, 8th and 10th weeks, respectively, indicating that histone H1 has a significant treatment effect for rheumatoid arthritis that is already in progress. Arthritis index in the comparison group that had the conventional dexamethasone treatment was 2.67, 1.67 and 3.00 at 7th, 8th and 10th weeks, respectively. (FIGS. 2A and 2B). Pictures of the fore feet of some of the mice were taken at 6th week after the administration of the collagen. Fore feet of the comparison group had edema, one of the symptoms of arthritis, whereas improvement of edema was observed in the test group that had the histone H1 treatment.

Estimation of Immune Reaction: Anti-Collagen Antibody Level

The anti-collagen,antibody level was measured to estimate the immune reaction as in EXAMPLE 3. The anti-collagen antibody level for the test group of the treatment effect was 0.540±170 ($p<0.00005$) which was significantly lower than the value of 0.925±075 for the comparison group. The biological significance, however, is not evident since the anti-collagen antibody level was relatively high in every group.

Pathological Observation by H-E Staining

Figure 4A:
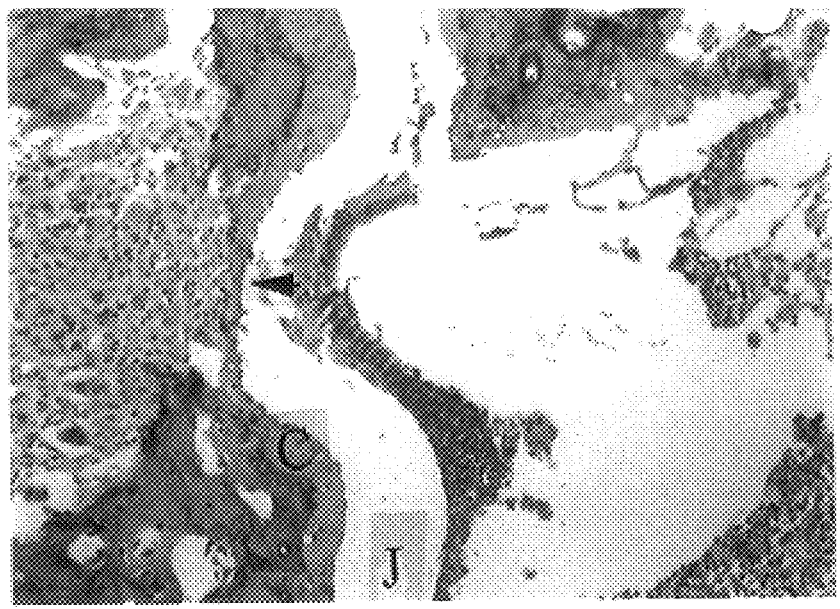
FIGS. 4A and 4B are the sections of knee joints of control group mice showing the formation of pannus, destruction of cartilage, bone erosion and manifestation of inflammatory cells at 10 weeks after the collagen antigen inoculation (P=pannus, C=cartilage, J=joint space).
Figure 4B:
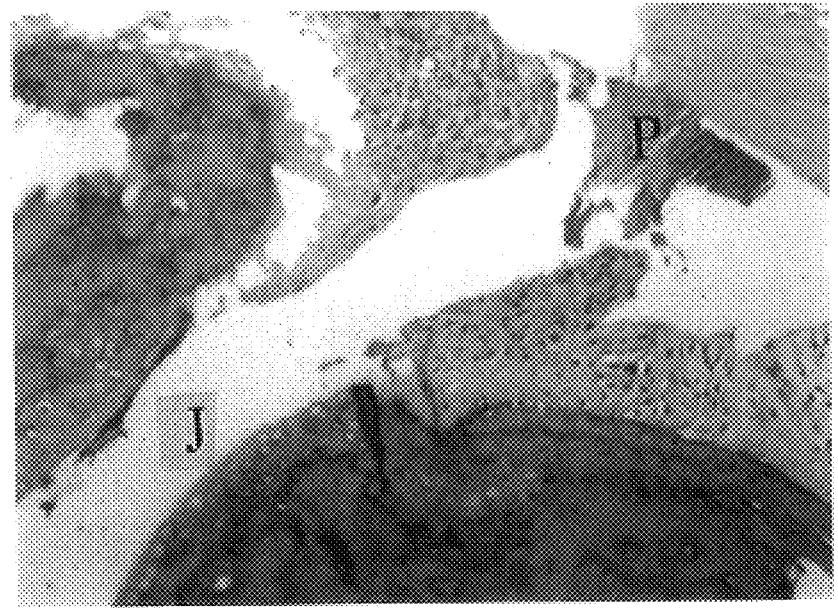

Mice were sacrificed by blood evacuation from the heart. The legs were cut immediately after the sacrifice and fixed in formalin. After the decalcification, legs were stained by hematoxylin-Eosin. The pathological observation by H-E staining showed that the formation of pannus, the erosion of cartilage and the manifestation of inflammatory cells were observed in 10 weeks after the antigen inoculation in the sections of the control group (FIGS. 4A and 4B; P=pannus, C=cartilage, J=joint space).

Figure 4C:
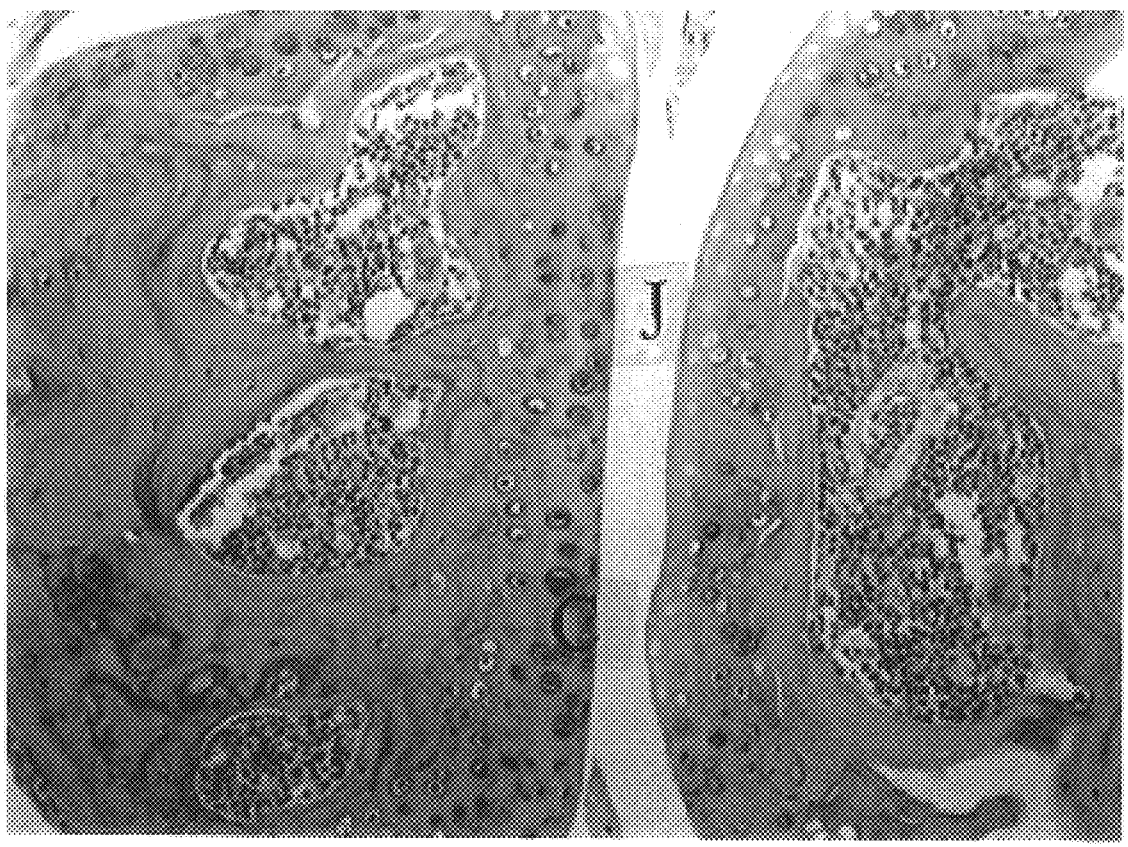
FIGS. 4C is a section of knee joint of a test group mouse that had histone H1 treatment at 10 weeks after the collagen antigen inoculation (P=pannus, C=cartilage, J=joint space).

In comparison, the formation of pannus, the erosion of cartilage or the manifestation of inflammatory cells were not observed in 10 weeks showing a normal tissue structure in the section of the test group that had the histone H1 treatment (FIG. 4C).

What is claimed is:

1. A method for reducing rheumatoid arthritis symptoms in patients comprising administering to said patients a composition containing a therapeutically effective amount of a histone.

2. The method of claim 1 wherein said histone is selected from the group consisting of H1, H2A, H2B, H3, H4, and a mixture thereof.

3. A method for preventing rheumatoid arthritis in patients comprising administering to said patients a composition containing a therapeutically effective amount of a histone.

4. The method of claim 3 wherein said histone is selected from the group consisting of H1, H2A, H2B, H3, H4, and a mixture thereof.

5. The method of claim 1 wherein said histone is histone H1.

6. The method of claim 3 wherein said histone is histone H1.

* * * * *